United States Patent
Chen et al.

(10) Patent No.: US 10,526,622 B2
(45) Date of Patent: Jan. 7, 2020

(54) PREPARATION METHOD FOR (R)-3-HYDROXYL-5-HEXENOATE

(71) Applicant: FUDAN UNIVERSITY, Shanghai (CN)

(72) Inventors: Fener Chen, Shanghai (CN); Zedu Huang, Shanghai (CN); Ge Meng, Shanghai (CN); Minjie Liu, Shanghai (CN); Zhining Li, Shanghai (CN); Zexu Wang, Shanghai (CN); Haihui Peng, Shanghai (CN); Fangjun Xiong, Shanghai (CN); Yan Wu, Shanghai (CN); Yuan Tao, Shanghai (CN)

(73) Assignee: Fudan University, Shanghai (CN)

( * ) Notice: Subject to any disclaimer, the term of this patent is extended or adjusted under 35 U.S.C. 154(b) by 78 days.

(21) Appl. No.: 15/871,039

(22) Filed: Jan. 14, 2018

(65) Prior Publication Data

US 2018/0340196 A1    Nov. 29, 2018

(30) Foreign Application Priority Data

May 26, 2017  (CN) .......................... 2017 1 0384245

(51) Int. Cl.
| | |
|---|---|
| C12P 7/62 | (2006.01) |
| C07C 69/732 | (2006.01) |
| C12N 9/04 | (2006.01) |
| C07C 67/28 | (2006.01) |
| G01N 30/02 | (2006.01) |

(52) U.S. Cl.
CPC ................ C12P 7/62 (2013.01); C07C 67/28 (2013.01); C07C 69/732 (2013.01); C12N 9/0006 (2013.01); *C12Y 101/0108* (2013.01); *G01N 2030/025* (2013.01)

(58) Field of Classification Search
None
See application file for complete search history.

(56) References Cited

U.S. PATENT DOCUMENTS 6,355,822 B1   3/2002  Johnson et al.

FOREIGN PATENT DOCUMENTS

| EP | 1176135 A1 | 1/2002 |
|---|---|---|
| WO | 2016074324 A1 | 5/2016 |

OTHER PUBLICATIONS

Stereoselective ketone reduction by a carbonyl reductase from Sporobolomyces salmonicolor. Substrate specificity, antioselectivity and enzyme-substrate docking studies† Dunming Zhu, (Year: 2006).*

Synthesis of ethyl-(3R,5S)-dihydroxy-6-benzyloxyhexanoates via diastereo- and enantioselective microbial reduction: Cloning and expression of ketoreductase III from Acinetobacter sp. SC 13874 Steven Goldberg (Year: 2008).*

N. Itoh . Purification and characterization of NADPH-dependent aldo—keto reductase specific for β-keto esters from Penicillium citrinum, (Year: 2004).*

Dunming Zhu et al. Stereoselective ketone reduction by a carbonyl reductase from Sporobolomyces salmonicolor. Substrate specificity, enantioselectivity and enzyme-substrate docking studies, Org. Biomol. Chem., 2006, 4, 2690-2695.

Goldberg et al. (Synthesis of ethyl-(3R, 5S)-dihydroxy-6-benzyloxyhexanoates via diastereo- and enantioselective microbial reduction: Cloning and expression of ketoreductase III from Acinetobacter sp. SC 13874 (Enzyme and Microbial Technology 43(7):544-549 Dec. 2008).

* cited by examiner

Primary Examiner — Kagnew H Gebreyesus
(74) Attorney, Agent, or Firm — Wayne & Ken, LLC; Tony Hom (57) ABSTRACT

The present disclosure relates to the technical field of biochemical engineering and particularly discloses a preparation method for (R)-3-hydroxyl-5-hexenoate. In the method of the present disclosure, the (R)-3-hydroxyl-5-hexenoate is prepared by catalytic reduction of 3-carbonyl-5-hexenoate by ketoreductase with 3-carbonyl-5-hexenoate as the substrate. The amino acid sequence of ketoreductase is shown in SEQ ID NO.1. In the present disclosure, the (R)-3-hydroxyl-5-hexenoate having a very high chiral purity is obtained by asymmetric reduction by ketoreductase as the biocatalyst. The present disclosure has the advantages of easy operation, mild reaction conditions, high reaction yield and good practical industrial application value.

8 Claims, 6 Drawing Sheets

Specification includes a Sequence Listing.

PREPARATION METHOD FOR (R)-3-HYDROXYL-5-HEXENOATE

REFERENCE TO AN ELECTRONIC SEQUENCE LISTING

The contents of the electronic sequence listing (Untitled_ST25.txt; Size: 5,000 bytes; and Date of Creation: Feb. 27, 2018) is herein incorporated by reference in its entirety.

TECHNICAL FIELD

The present disclosure belongs to the technical field of biochemical engineering and particularly relates to a preparation method for (R)-3-hydroxyl-5-hexenoate.

BACKGROUND

As an important chiral compound, (R)-3-hydroxyl-5-hexenoate has the following chemical formula (I), where R is alkyl or cycloalkyl having 1 to 8 carbon atoms, or mono- or poly-substituted aryl or aralkyl. The compound (I) has been widely used for synthesizing chemical and chemical intermediates. For example, Chen Fener et al. (WO2016074324) disclosed an efficient route for preparing, from derivatives of the compound (1), a key chemical intermediate (III) in synthesis of statin antilipemic agents.

It is indicated by document retrieval that chemical methods are main ways of synthesizing the compound (I) and structural analogues thereof at present. For example, U.S. Pat. No. 6,355,822 disclosed a method for stereoselectively preparing 3-hydroxyl-5-hexenoate (I) by reduction of a structural analogue 3-carbonyl-5-hexenoate (II) by using the resulting product of in-situ reaction of L-tartaric acid with sodium borohydride as chiral reductant. The reduction reaction needs to be conducted at a low temperature (−20° C. to −50° C.). Such reaction condition is strict, and the practical industrial application prospect is limited.

European Patent EP1176135 disclosed a preparation method for corresponding optically pure structural analogue 3-hydroxyl-5-hexenoate (I) by asymmetric catalyzation and hydrogenation of structural analogue 3-carbonyl-5-hexenoate (II) by using a complex of ruthenium and chiral phosphine ligand. Since this reaction needs to be conducted at a high temperature and under a high hydrogen pressure, it is inconvenient for industrial production.

It was yet reported that (R)-3-hydroxyl-5-hexenoate is selectively generated by biological catalysis. For example, referring to J. Chem. Soc. Perkin. Trans. 1, 1991, 133-140, it was reported that (R)-3-hydroxyl-5-hexenoate (1) was selectively generated by catalytic reduction of the compound (II) by baker's yeast, where the ee value was 78% (methyl ester) and 43% (ethyl ester). This method is less stereoselective and is not applicable to industrial production.

SUMMARY

An objective of the present disclosure is to provide a preparation method for (R)-3-hydroxyl-5-hexenoate, which is high in product yield, excellent in stereoselectivity and environmentally-friendly.

The (R)-3-hydroxyl-5-hexenoate has the following chemical formula (I):

where R is alkyl or cycloalkyl having 1 to 8 carbon atoms, or mono- or poly-substituted aryl or aralkyl.

In the preparation method for (R)-3-hydroxyl-5-hexenoate provided by the present disclosure, the (R)-3-hydroxyl-5-hexenoate (I) is obtained by catalytic reduction of 3-carbonyl-5-hexenoate by ketoreductase with 3-carbonyl-5-hexenoate as the substrate.

The amino acid sequence of the ketoreductase is shown in SEQ ID NO.1, or is a mutated amino acid sequence which is obtained by insertion, deletion or substitution of at least one amino acid in the amino acid sequence shown in SEQ ID NO.1 under the premise of keeping the catalytic activity of the ketoreductase.

Coenzyme NADP+ can be further added in the reaction system.

Preferably, the dosage of the NADP+ is 0.005% to 0.01% of the dosage (w/w) of the substrate.

The reaction system further includes a regeneration system of coenzyme NADPH.

The regeneration system of coenzyme NADPH in the reaction system can be any existing system for regenerating NADPH in the art. Preferably, the coenzyme NADPH is regenerated by the joint use of isopropanol and isopropanol dehydrogenase. More preferably, the regeneration system is isopropanol dehydrogenase having an amino acid sequence shown in SEQ ID NO.2 or a mutated amino acid sequence which is obtained by insertion, deletion or substitution of at least one amino acid in the amino acid sequence shown in SEQ ID NO.2 under the premise of keeping the catalytic activity of the isopropanol dehydrogenase.

The synthetic route of the reaction is as follows:

wherein R is alkyl or cycloalkyl having 1 to 8 carbon atoms, or mono- or poly-substituted aryl or aralkyl.

Both the amino acid sequence of the ketoreductase and the amino acid sequence of the isopropanol dehydrogenase can be prepared by the synthesis of the commercially available whole-genome.

The stereocenter of the (R)-3-hydroxyl-5-hexenoate obtained by catalytic reduction of substrate by the ketoreductase is R configuration.

In the present disclosure, both the ketoreductase and the isopropanol dehydrogenase can be prepared by conventional technical means in the art, specifically: a gene fragment containing ketoreductase genes or isopropanol dehydrogenase genes is linked to enzyme-digested products of pET-24b or pET-22b plasmid, and then transferred to competent *E. coli* JM109(DE3) strains to obtain a transformed recombinant; and, the recombinant is inducibly expressed, the cells are disrupted and centrifuged, and the supernatant is collected to obtain ketoreductase and isopropanol dehydrogenase.

Preferably, in the initial reaction system, the concentration percentage by mass of the substrate is 1% to 20% (w/v), more preferably 5% to 15%.

The dosage of the ketoreductase (by wet cell weight) is 1% to 30% of the mass of the substrate, more preferably 20% to 30/o %.

The dosage of the isopropanol dehydrogenase (by wet cell weight) is 1% to 15% of the mass of the substrate, more preferably 10% to 15%.

Preferably, the reaction temperature is 15° C. to 35° C., more preferably 25° C. to 30° C.; and the reaction time is 2 to 18 hours.

Preferably, the pH value of the reaction solution is 6 to 9, more preferably 7 to 8.

Preferably, in the initial reaction system, the concentration percentage of isopropanol is 5% to 20% (v/v), more preferably 10% to 20%.

At the end of the reaction, the reaction solution is subjected to after treatment to obtain the finished product. Specifically, silica gel is added in the reaction solution, stirred for 15 mins, and filtered; the filter cake is washed with ethyl acetate; the filtrate is layered; and the aqueous layer is extracted twice with ethyl acetate. The organic layer is collected, washed respectively with water and saturated brine, dried with anhydrous sodium sulfate, and concentrated under a reduced pressure to obtain a dry product.

Compared with the prior art, the present disclosure has the following beneficial effects:

easy operation, mild reaction conditions, high reaction yield, excellent stereoselectivity, environmental friendliness, and high practical industrial application value.

DETAILED DESCRIPTION OF THE DISCLOSURE

The present disclosure will be further described by specific embodiments. But the present disclosure is not limited thereto.

Embodiment 1: Production of Crude Ketoreductase Enzyme Solution in a Fermenter

A gene fragment containing ketoreductase genes was linked to enzyme-digested products of the pET-24b plasmid, and transferred to competent *E. coli* JM109(DE3) strains. Positive clones were selected and inoculated to 5 mL of liquid LB culture medium containing kanamycin for activation for 8 hours (37° C., 180 rpm).

The activated culture was inoculated, in an inoculation size of 1/100, to 50 mL of liquid LB culture medium containing kanamycin for culturing overnight (37° C., 180 rpm).

The overnight-cultured culture was inoculated, in an inoculation size of 1/100, to 5 L of liquid culture medium (in a 7 L fermenter, containing 2% of tryptone, 1% of yeast powder, and 1% NaCl) containing kanamycin (100 mg) for fermented culturing (30° C., 300 rpm) until $OD_{600}$ reaches 10, added with IPTG (50 mg), and cultured overnight at 25° C. (during which, glycerin was supplemented and the pH value was controlled at 6.8). Cells (wet cells) were collected centrifugally, and suspended with 1.2 L of phosphate buffer (100 mM, pH7.5). The cells were disrupted by a high-pressure cell disrupter (800 bar), and centrifuged. The supernatant was the crude ketoreductase enzyme solution.

Embodiment 2: Production of Isopropanol Dehydrogenase in a Fermenter

A gene fragment containing isopropanol dehydrogenase genes was linked to enzyme-digested products of the pET-22b plasmid, and transferred to competent *E. coli* JM109 (DE3) strains. Positive clones were selected and inoculated to 5 mL of liquid LB culture medium containing ampicillin for activation for 8 hours (37° C., 180 rpm).

The activated culture was inoculated, in an inoculation size of 1/100, to 50 mL of liquid LB culture medium containing ampicillin for culturing overnight (37° C., 180 rpm).

The overnight-cultured culture was inoculated, in an inoculation size of 1/100, to 5 L of liquid culture medium (in a 7 L fermenter, containing 2% of tryptone, 1% of yeast powder, and 1% NaCl) containing ampicillin (100 mg) for fermented culturing (30° C., 300 rpm) until $OD_{600}$ reaches 10, added with IPTG (50 mg), and cultured overnight at 25° C. (during which, glycerin was supplemented and the pH value was controlled at 6.8). Cells (wet cells) were collected centrifugally, and suspended with 1.2 L of phosphate buffer (100 mM, pH7.5). The cells were disrupted by a high-pressure cell disrupter (800 bar), and centrifuged. The supernatant was the crude isopropanol dehydrogenase enzyme solution.

Embodiment 3: Generation of (R)-3-hydroxy-5-methyl Hexenoate (Hectogram) by Asymmetric Reduction by Ketoreductase as Catalyst 0.5 L of phosphate buffer (100 mM, pH7.5) and 0.1 L of isopropanol were added in a reaction flask (2 L), mixed uniformly, added with 0.2 L of the crude ketoreductase enzyme solution obtained in Embodiment 1 and 0. IL of the crude isopropanol dehydrogenase enzyme solution obtained in Embodiment 2, then added with 5 mg of coenzyme NADP+, and finally added with 100 g of 3-carbonyl-5-methyl hexenoate as substrate. The reaction was conducted at 30° C. and monitored by a GC-MS (Gas Chromatography-Mass Spectrometer). 16 hours later, the conversion rate of products is greater than 99%. Then, the reaction was terminated.

Silica gel was added in the reaction liquid, stirred for 15 mins, and filtered; the filter cake was washed with ethyl acetate; the filtrate was layered; and the aqueous layer was extracted twice with ethyl acetate. The organic layer was collected, washed respectively with water and saturated brine, dried with anhydrous sodium sulfate, and concentrated under a reduced pressure to obtain a dry product 87.2 g (with a yield of 86.0% and an ee value of 99.9%). $^1$H NMR (CDCl$_3$, 400 MHz): δ/ppm 5.85 (m, 1H), 5.16 (d, J=6.4 Hz, 1H), 5.12 (s, 1H), 4.06 (m, 1H), 3.79 (s, 3H), 2.50-2.21 (m, 4H).

Embodiment 4: Generation of (R)-3-hydroxy-5-ethyl Hexenoate (Hectogram) by Asymmetric Reduction by Ketoreductase as Catalyst 0.55 L of phosphate buffer (100 mM, pH7.5) and 0.15 L of isopropanol were added in a reaction flask (2 L), mixed uniformly, added with 0.1 L of the crude ketoreductase enzyme solution obtained in Embodiment 1 and 0.1 L of the crude isopropanol dehydrogenase enzyme solution obtained in Embodiment 2, then added with 10 mg of coenzyme NADP+, and finally added with 100 g of 3-carbonyl-5-ethyl hexenoate as substrate. The reaction was conducted at 30° C. and monitored by a GC-MS (Gas Chromatography-Mass Spectrometer). 14 hours later, the conversion rate of products is greater than 99%. Then, the reaction was terminated.

Silica gel was added in the reaction liquid, stirred for 15 mins, and filtered; the filter cake was washed with ethyl acetate: the filtrate was layered; and the aqueous layer was extracted twice with ethyl acetate. The organic layer was collected, washed respectively with water and saturated brine, dried with anhydrous sodium sulfate, and concentrated under a reduced pressure to obtain a dry product 89.4 g (with a yield of 88.3% and an ee value of 99.9%). $^1$H NMR (CDCl$_3$, 400 MHz): δ/ppm 5.86 (m, 1H), 5.15 (d, J=6.4 Hz, 1H), 5.11 (s, 1H), 4.18 (q, J=7.2 Hz, 2H), 4.04 (m, 1H), 2.52-2.20 (m, 4H), 1.28 (t, J=7.2 Hz, 3H).

Embodiment 5: Generation of (R)-3-hydroxy-5-cyclopropyl Hexenoate (Decagram) by Asymmetric Reduction by Ketoreductase as Catalyst 55 mL of phosphate buffer (100 mM, pH7.5) and 15 mL of isopropanol were added in a reaction flask (250 mL), mixed uniformly, added with 15 mL of the crude ketoreductase enzyme solution obtained in Embodiment 1 and 5 mL of the crude isopropanol dehydrogenase enzyme solution obtained in Embodiment 2, then added with 1 mg of coenzyme NADP+, and finally added with 10 g of 3-carbonyl-5-cyclopropyl hexenoate as substrate. The reaction was conducted at 25° C. and monitored by a GC-MS (Gas Chromatography-Mass Spectrometer). 16 hours later, the conversion rate of products is greater than 97%. Then, the reaction was terminated.

Silica gel was added in the reaction liquid, stirred for 15 mins, and filtered; the filter cake was washed with ethyl acetate; the filtrate was layered; and the aqueous layer was extracted twice with ethyl acetate. The organic layer was collected, washed respectively with water and saturated brine, dried with anhydrous sodium sulfate, and concentrated under a reduced pressure to obtain a dry product 8.1 g (with a yield of 80.0% and an ee value of 99.8%). $^1$H NMR (CDCl$_3$, 400 MHz): δ/ppm 5.88 (m, 1H), 5.19 (d, J=6.4 Hz, 1H), 5.07 (s, 1H), 4.06 (m, 1H), 3.58 (m, 1H), 2.51-2.18 (m, 4H), 0.62 (m, 2H), 0.37 (m, 2H).

Figure 1:
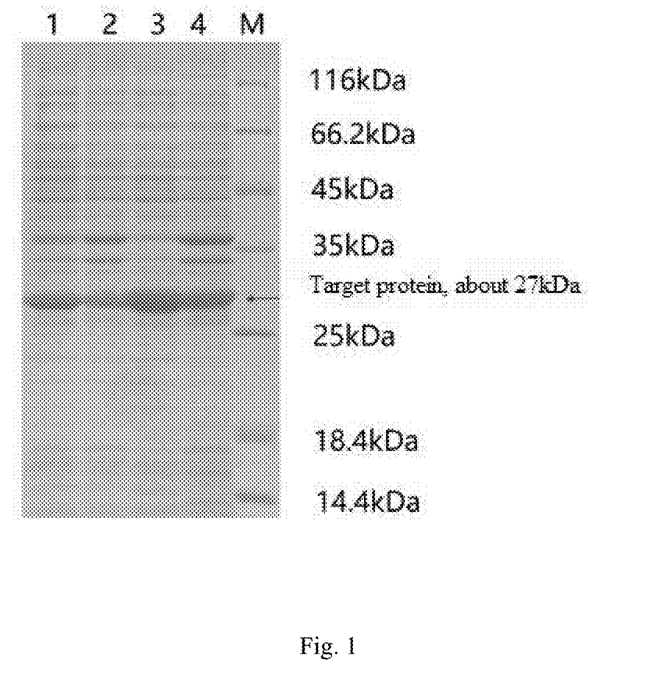
FIG. 1 is an SDS-PAGE electrophoretogram of protein inducibly expressed by ketoreductase and isopropanol dehydrogenase, where M denotes a protein marker, 1 denotes the supernatant of disrupted cells induced by the ketoreductase, 2 denotes the precipitate of disrupted cells induced by the ketoreductase, 3 denotes of the supernatant of disrupted cells induced by the isopropanol dehydrogenase, and 4 denotes the precipitate of disrupted cells induced by the isopropanol dehydrogenase.
Figure 2:
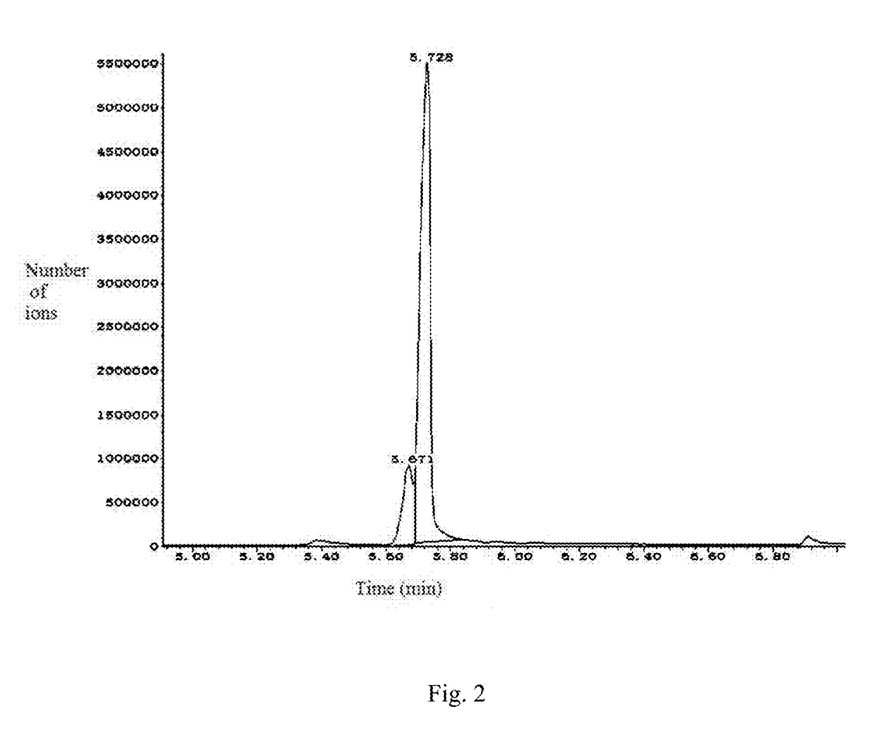
FIG. 2 is a GC-MS (TIC) graph of samples after 1 hour of reaction in Embodiment 3 of the present disclosure.
Figure 3:
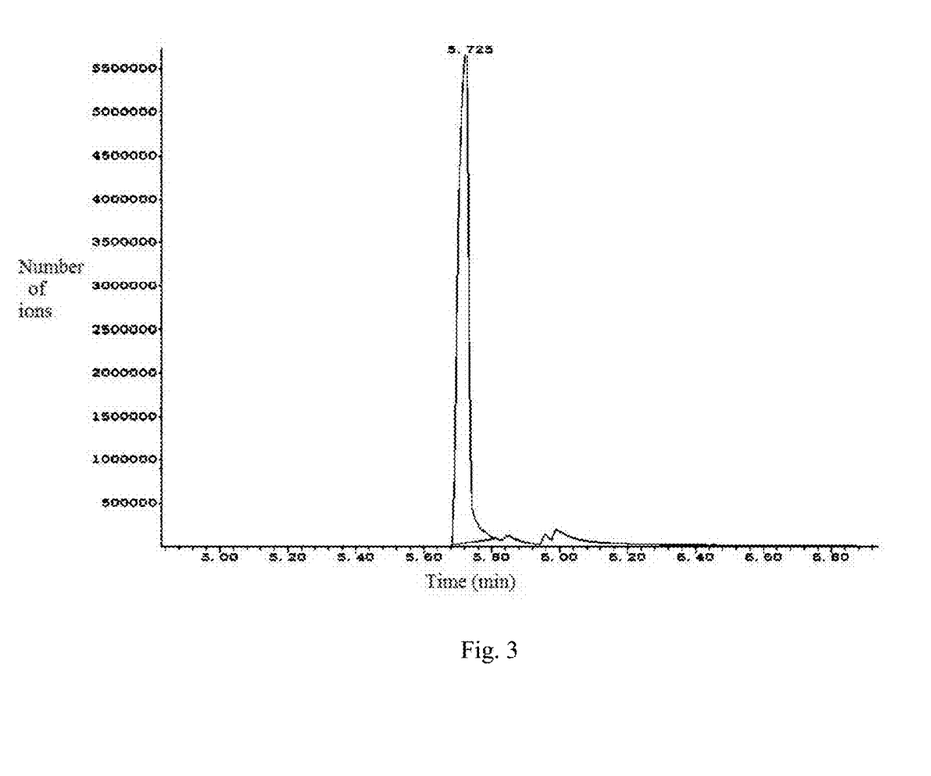
FIG. 3 is a GC-MS (TIC) graph of samples after 16 hours of reaction in Embodiment 3 of the present disclosure.
Figure 4:
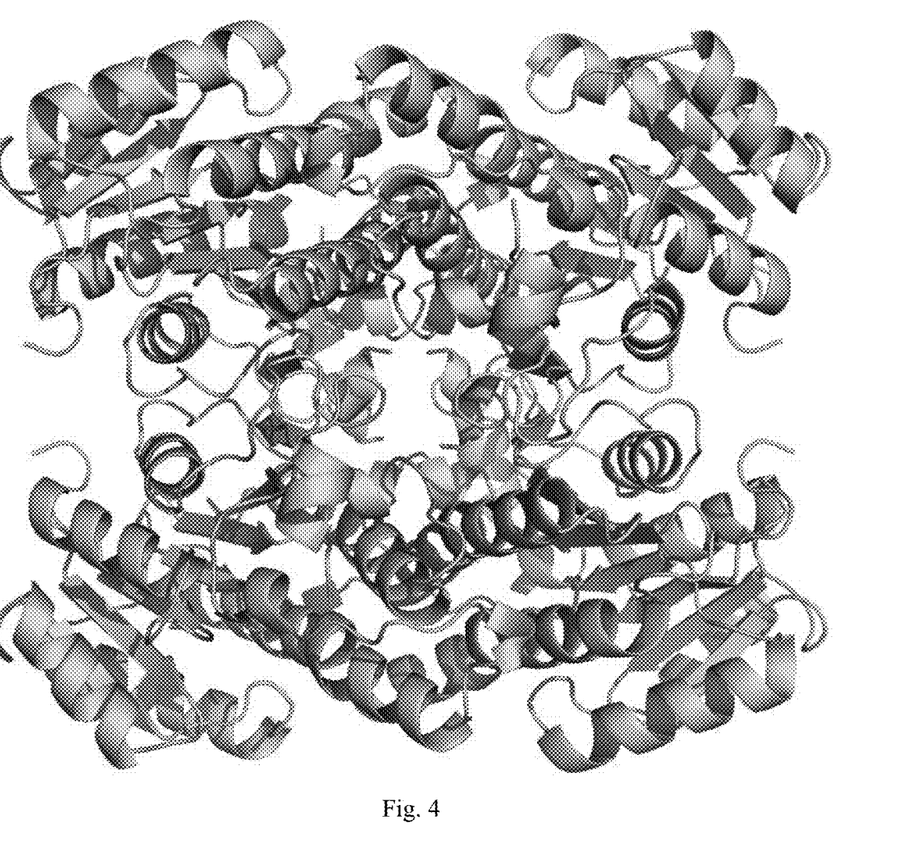
FIG. 4 is a 3D structural diagram after homologous modeling by a computer according to SEQ ID NO.1.
Figure 5:
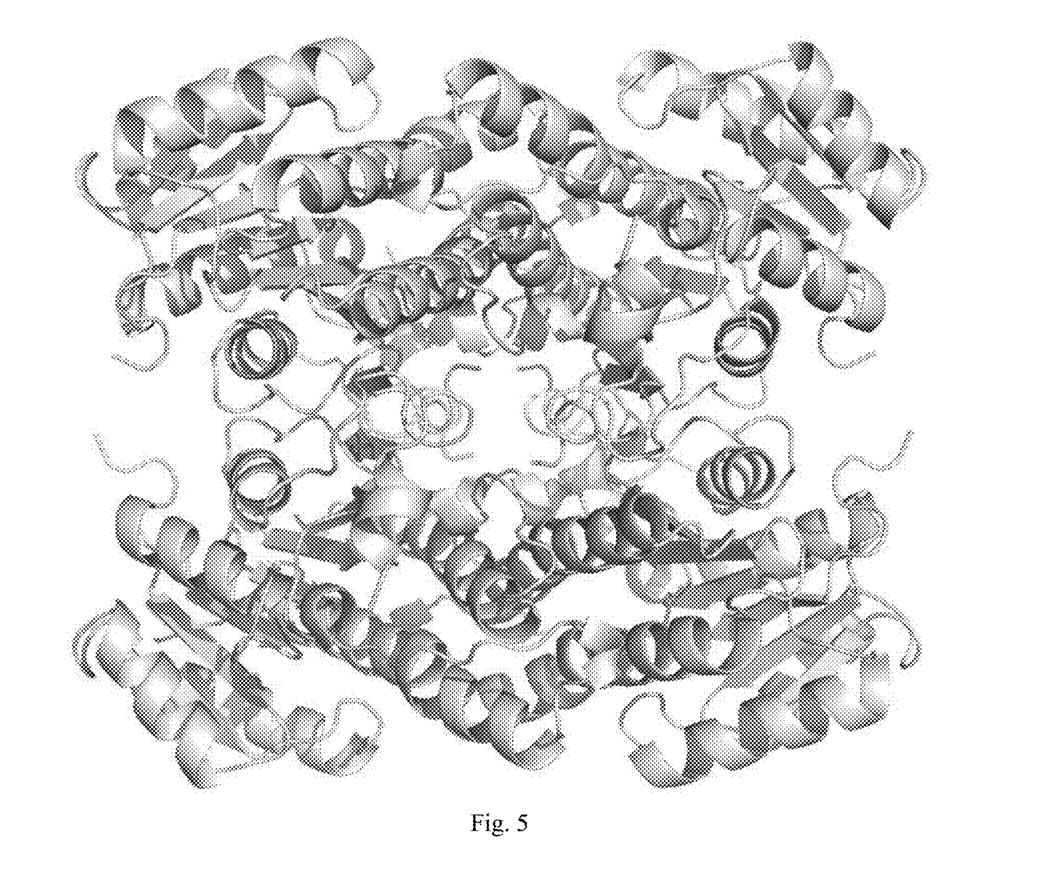
FIG. 5 is a 3D structural diagram after homologous modeling by a computer according to SEQ ID NO.2.
Figure 6:
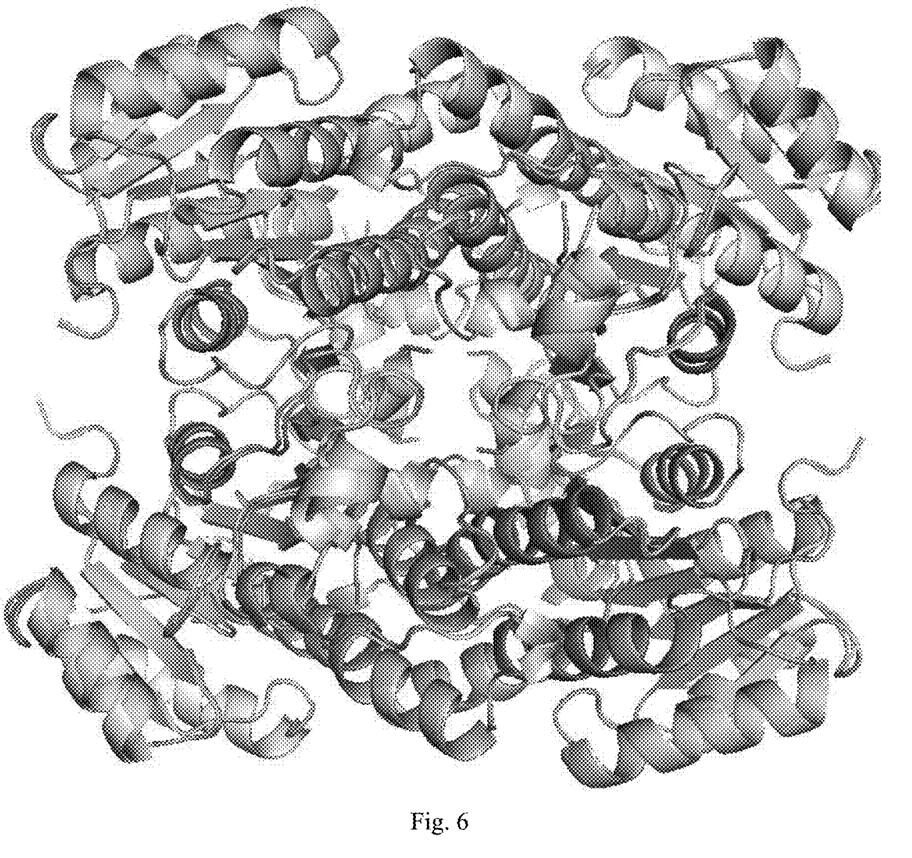
FIG. 6 is a 3D structural superposition diagram after homologous modeling by a computer according to SEQ ID NO. 1 and SEQ ID NO.2.

As shown in FIG. 4 to FIG. 5, the three-dimensional structures of the two the major enzyme chain were obtained by computational homologous modeling. The alignment of these two enzyme showed that they are quite similar in overall shape as shown in FIG. 6, except for some minor difference in the loop around the different amino acid residues between the two chains. For example, valine (Val) 199 in FIG. 4 and leucine (Leu) 199 in FIG. 5 results in the slightly difference in loops in the vicinity of these amino acids. Those structural analyses and contrast will contribute to improving the structure and function of enzymes.

The foregoing description merely shows preferred embodiments of the present disclosure and is only intended to explain the technical concepts and features of the present disclosure. The purpose is to enable a person of ordinary skill in the art to understand and thus practice the present disclosure. It is not intended to limit the protection scope of the present disclosure. Any modifications, equivalent replacements, improvements and the like within the spirit and principle of the present disclosure shall be included in the protection scope of the present disclosure.

What is claimed is:

1. A method for preparing (R)-3-hydroxy-5-hexanoate, comprising:

subjecting 3-carbonyl-5-hexanoate (II) to asymmetric reduction in the presence of the ketoreductase of SEQ ID NO: 1 as a catalyst to produce (R)-3-hydroxy-5-hexanoate (I), as shown in the following reaction scheme:

wherein R is alkyl or cycloalkyl having 1 to 8 carbon atoms, or mono- or poly-substituted aryl or aralkyl.

2. The method according to claim 1, wherein coenzyme NADP+ is further added in a reaction system, and a dosage of the NADP+ is 0.005% to 0.01% of a dosage (w/w) of the 3-carbonyl-5-hexenoate (II).

3. The method according to claim 2, wherein the reaction system further comprises a regeneration system for regenerating NADPH from the NADP+.

4. The method according to claim 3, wherein the regeneration system of the NADPH in the reaction system is isopropanol dehydrogenase having an amino acid sequence shown in SEQ ID NO: 2.

5. The method according to claim 4, wherein in an initial reaction system, a concentration percentage by mass of the 3-carbonyl-5-hexenoate (II) is 1% to 20%; the dosage of the ketoreductase by wet cell weight is 1% to 30% of the mass of the 3-carbonyl-5-hexenoate (II), and the dosage of the isopropanol dehydrogenase by wet cell weight is 1% to 15% of the mass of the 3-carbonyl-5-hexenoate (II).

6. The method according to claim 1, wherein a reaction temperature is 15° C. to 35° C.

7. The method according to claim 6, wherein a pH value of the reaction system is 6 to 9.

8. The method according to claim 1, wherein the initial reaction system further comprises isopropanol, and a concentration percentage of the isopropanol is 5% to 20% (v/v).

\* \* \* \* \*

SEQUENCE LISTING

```
<160> NUMBER OF SEQ ID NOS: 2

<210> SEQ ID NO 1
<211> LENGTH: 252
<212> TYPE: PRT
<213> ORGANISM: Artificial Sequence
<220> FEATURE:
<223> OTHER INFORMATION: Synthetic

<400> SEQUENCE: 1
```

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Arg Ala Ala
        35                  40                  45

Lys Ser Ile Gly Gly Thr Asp Val Ile Arg Phe Ile Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Asp Val Val
                85                  90                  95

Lys Ser Val Glu Asp Thr Thr Glu Glu Trp His Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
    130                 135                 140

Phe Gly Met Val Gly Asp Pro Thr Val Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Val Glu Gly Ala Glu Met Trp Ser Gln
    195                 200                 205

Arg Thr Lys Thr Pro Met Gly His Ile Gly Glu Pro Asn Asp Ile Ala
    210                 215                 220

Trp Val Cys Val Tyr Leu Ala Ser Gly Glu Ser Lys Phe Ala Thr Gly
225                 230                 235                 240

Ala Glu Phe Val Ile Asp Gly Gly Trp Thr Ala Gln
                245                 250
```

<210> SEQ ID NO 2
<211> LENGTH: 252
<212> TYPE: PRT
<213> ORGANISM: Artificial Sequence
<220> FEATURE:
<223> OTHER INFORMATION: synthetic

<400> SEQUENCE: 2

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Glu Glu Trp Arg Lys Leu Leu Ser
            100                 105                 110
```

```
Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```